(12) United States Patent
Martel

(10) Patent No.: US 10,076,375 B1
(45) Date of Patent: Sep. 18, 2018

(54) IMPLANTABLE DEVICE FACILITATING ROTATIONAL-GUIDED GROWTH AND METHOD OF USE

(71) Applicant: Gonzalo Alfredo Martel, Salta (AR)

(72) Inventor: Gonzalo Alfredo Martel, Salta (AR)

( * ) Notice: Subject to any disclaimer, the term of this patent is extended or adjusted under 35 U.S.C. 154(b) by 267 days.

(21) Appl. No.: 15/055,288

(22) Filed: Feb. 26, 2016

(51) Int. Cl.
*A61B 17/88* (2006.01)
*A61B 17/84* (2006.01)
*A61B 17/86* (2006.01)
*A61B 17/56* (2006.01)
*A61B 17/68* (2006.01)

(52) U.S. Cl.
CPC ............ *A61B 17/88* (2013.01); *A61B 17/842* (2013.01); *A61B 17/864* (2013.01); *A61B 2017/564* (2013.01); *A61B 2017/681* (2013.01)

(58) Field of Classification Search
CPC .................................................... A61B 17/842
See application file for complete search history.

(56) References Cited

U.S. PATENT DOCUMENTS 6,368,326 B1 * 4/2002 Dakin .................. A61B 17/683
606/103

* cited by examiner

*Primary Examiner* — Andrew Yang
(74) *Attorney, Agent, or Firm* — Sanchelima & Associates, P.A.; Christian Sanchelima; Jesus Sanchelima

(57) ABSTRACT

An implantable device for controlling rotational growth is disclosed. The implantable device comprises a first screw and a second screw inserted using minimally invasive surgical procedures and positioned within holes created by guiding members. The first screw is positioned in an metaphyseal section and the second screw is positioned in a epiphyseal section in distal femur. The implantable device comprises a cable drawn through the first screw and the second screw. Further, the implantable device comprises a cotter or a thin screw inserted in the first screw to lock the cable. The implantable device modifies longitudinal growth and generates rotational movement due to torque generation, thereby promoting the rotational growth of the bone.

3 Claims, 6 Drawing Sheets

IMPLANTABLE DEVICE FACILITATING ROTATIONAL-GUIDED GROWTH AND METHOD OF USE

FIELD OF INVENTION

The present disclosure relates to a field of treating rotational deformities. More specifically, the present disclosure relates to an implantable device, which allows to treat rotational deformities with mini-invasive surgery.

BACKGROUND

As known, rotational deformities of femur and tibia are some of the common orthopedic alignment problems in lower extremity for subjects such as children. The rotational alignment problems include in-toeing and out-toeing. Typically, limbs alignment problems are treated by orthopedic surgeons. Generally, the pediatric orthopedic surgeons treat mild deformities by suggesting the children to avoid sitting in reverse W position for internal femoral torsion and external tibial torsion. Further, a variety of devices are used to treat the orthopedic alignment problems. For example, a device to impart rotational torque to lower limbs and bars for internal tibial torsion to twister cables for internal femoral torsion is used. In more severe cases cuts in the bone are made to set the bones in a correct position and internal implants (plates, nails, casts) are used to hold the bone pieces together until the bone heals.

The rotational deformity is associated with conditions such as miserable misalignment syndrome, cerebral palsy, artrogriposis and other conditions. Lack of rotation in one direction leads to pain at back, hip or knee due to alteration of gait and compensatory motion at the joints. Further, the rotational deformity leads to changes in lower back, hip, knee, patella-femoral and ankle joints.

SUMMARY

The above-mentioned problems are addressed by providing an implantable device to control axial rotation deformities.

In one example, an implantable device comprises a first screw and a second screw. Each of the first screw and the second screw comprise a hollow structure and an opening at each distal end. The first screw and second screw are placed one on top of the other at predetermined distances and at a predetermined cross-angle depending on the rotational correction needed. In other words, the first screw and the second screw are positioned longitudinally opposite to each other. The first screw is positioned in a metaphyseal section and the second screw is positioned in an epiphyseal section in the femur. The first screw and the second screw are coupled by inserting a cable through the respective hollow structure. Further, the cable is locked in the hollow structure of the first screw by inserting a cotter or a thin screw, thereby locking the cable in place. The implantable device is used to facilitate guide growth to correct axial rotation deformities. In frontal or sagittal plane angular deformity, the cable acts as a tether growth at one periphery of physis. As the first screw and the second screw are positioned in a cross shape configuration across the axial plane including a cable that crosses the growth plate in inclined opposite directions at two opposite peripheries of the physis, a rotational tether is imparted on the physis.

The features and advantages described in this summary and in the following detailed description are not all-inclusive, and particularly, many additional features and advantages will be apparent to one of ordinary skill in the relevant art, in view of the drawings, and specification thereof. Moreover, it should be noted that the language used in the specification has been principally selected for readability and instructional purposes, and may not have been selected to delineate or circumscribe the inventive subject matter.

BRIEF DESCRIPTION OF DRAWINGS

In the following drawings, like reference numbers are used to refer to like elements. Although the following figures depict various examples of the invention, the invention is not limited to the examples depicted in the figures.

DETAILED DESCRIPTION

In the present disclosure, relational terms such as first and second, and the like, may be used to distinguish one entity from the other, without necessarily implying any actual relationship or order between such entities. The following detailed description is intended to provide example implementations to one of ordinary skill in the art, and is not intended to limit the invention to the explicit disclosure, as one or ordinary skill in the art will understand that variations can be substituted that are within the scope of the invention as described.

The present disclosure discloses an implantable device for controlling rotational or angular deformities in subjects such as children. The implantable device is used to correct the angular and rotational deformities of lower limbs in children and adolescents by guided growth using crossing hallowed screws connected using a cable assembly. The implantable device comprises a first screw and a second screw. Each of the first screw and the second screw comprise a hollow structure. The first screw is positioned in a metaphyseal section and the second screw is positioned in an epiphyseal section in the distal femur. Alternatively, the first and second screws can be positions in the tibia's epiphyseal and metaphyseal sections, respectively. This system can be implemented in a similar way for other bones of the body. The first screw and the second screw are coupled by inserting a cable or a flexible material through the respective hollow structure. Further, the cable is locked in the hollow structure of the first screw by inserting a cotter or a thin locking screw. The various embodiments for correcting rotational deformities in subjects are explained in conjunction with the description of FIGS. 1-7.

Figure 1:
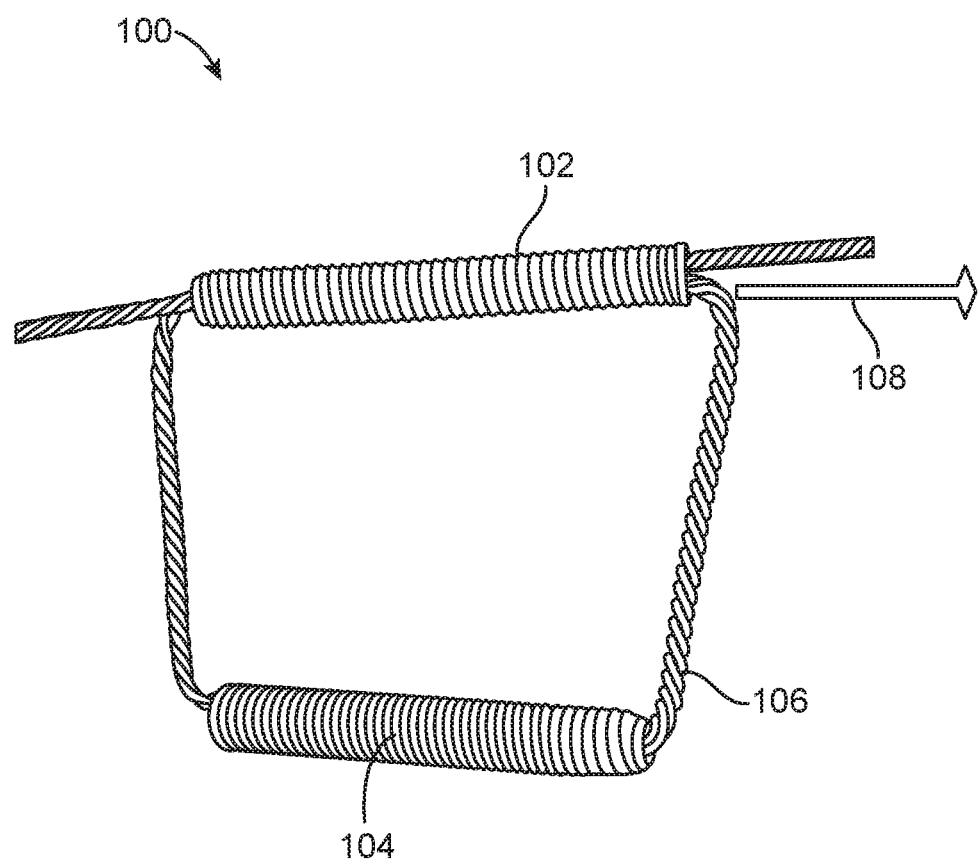
FIG. 1 illustrates an implantable device for controlling axial rotation deformities, in accordance with one embodiment 100 of the present disclosure, showing first screw 102, second screw 104, cable 106, and cotter 108.

Referring to FIG. 1, an implantable device 100 used to correct angular deformities is shown, in accordance with one embodiment of the present disclosure. The implantable device 100 comprises a hollowed, metaphyseal screw 102 and a epiphyseal screw 104. In one example, screw 102 may be a metaphyseal screw. In one example, screw 104 may be an epiphyseal screw. Each of the metaphyseal screw 102 and the epiphyseal screw 104 comprises a hollow structure with an opening on opposite distal ends. In one embodiment, the metaphyseal screw 102 and the epiphyseal screw 104 may have a thickness or outer diameter of 5 millimeter (mm). Further, the hole may have a thickness of 3 millimeter (mm). The epiphyseal screw 104 may have an outer diameter of 4 mm and an inner diameter of 2 mm.

Although the present disclosure discloses a threaded screw, it should be understood that different designs that are well known in the art can be used for metaphyseal screw 102 and epiphyseal screw 104.

The implantable device 100 may further comprise a flexible rope or cable 106. In one embodiment, the cable 106 may have a thickness of 1.5 mm. In another embodiment, the cable 106 may have a thickness range between 1.5 mm-2.5 mm. The cable 106 may be drawn through the hollow structure of the metaphyseal screw 102 and the epiphyseal screw 104. The implantable device 100 further comprises a cotter or a thin screw 108 to be inserted at one end of the metaphyseal screw 102 to lock in the cable 106 as shown in FIG. 1. In one embodiment, the cotter or thin screw 108 may have a thickness of 1.0 mm-2.5 mm. It should be understood that the cotter 108 may be inserted through the hollow structure of the metaphyseal screw 102 to lock both ends of the cable 106 and such implementation is within the scope of the present disclosure.

Figure 2:
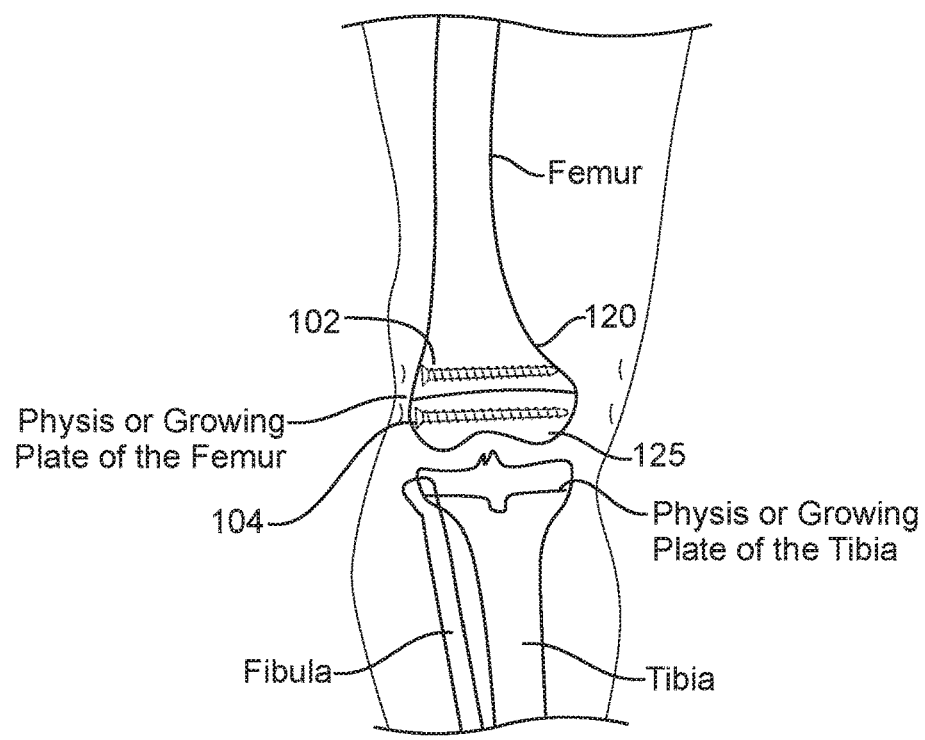
FIG. 2 is a schematic anterior view of a human joint showing a first screw inserted into the metaphysis section 120 of the femur and a second screw inserted in the epiphysis section 125 parallel and spaced apart by the physis or growth plate, in accordance with one embodiment of the present disclosure.
Figure 3:
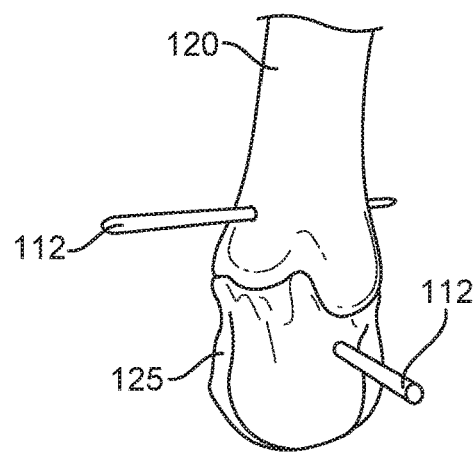
FIG. 3 illustrates direction placement of the guide members 112 for the first screw 102 and the second screw 104, in accordance with one embodiment of the present disclosure, these guide members 112 are used as a guide for the drill to set screws 102 104.

Referring to FIG. 2, a schematic anterior view of human joint is shown. As can be seen from the FIG. 2, a distal femur is proximal to a tibia and a fibula. Further, a distal femoral physis or growth plate separates a metaphyphyseal section 120 from an epiphyseal section 125 of the distal femur. Referring to FIG. 2 and FIG. 3, placement of the metaphyseal screw 102 and the epiphyseal screw 104 in the metaphysical section 120 and the epiphyseal section 125, respectively is shown using guiding members 112, respectively. In order to insert the metaphyseal screw 102, a guiding hole is made using guiding member 112 in the metaphyseal section 120. Similarly, a hole is made in the epiphyseal section 125 using guiding member 112 to insert the epiphyseal screw 104. The holes in the metaphyseal section 120 and the epiphyseal section 125 may be made using a cannulated drill. The metaphyseal screw 102 and the epiphyseal screw 104 are placed at a fixed crossing angle in an axial plane. For example, the metaphyseal screw 102 and the epiphyseal screw 104 may be placed at an angle of between 35 and 55 degrees.

Figure 4A:
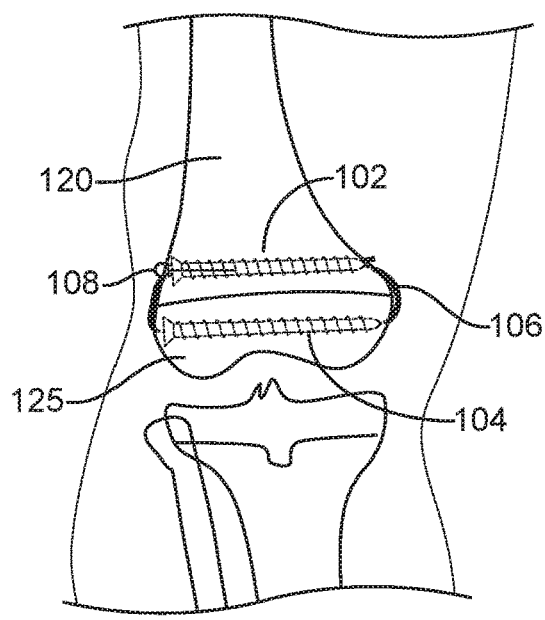
FIG. 4A illustrates a front elevational partial view of a patient's knee showing cable 106 passed through first screw 102 and second screw 104 and using cotter 108 or a thin screw to lock cable 106 in place, in accordance with one embodiment of the present disclosure.
Figure 4B:
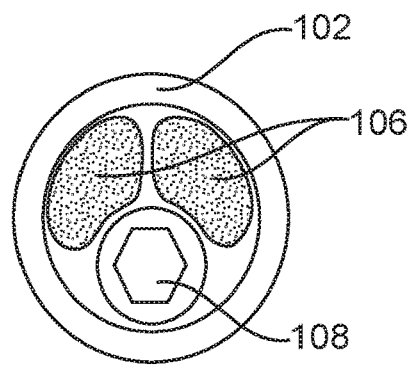
FIG. 4B shows a cross-section view of hollow screw 102 showing cable 106 passed through twice within and cotter 108 locking cable 106 in place inside screw 102.
Figure 4C:
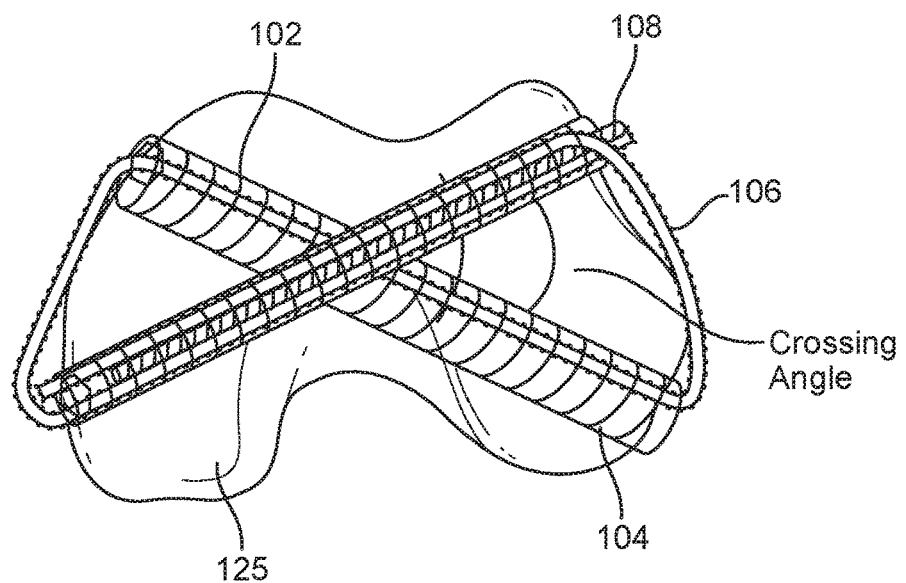
FIG. 4C illustrates an bottom view of the femur showing first and second hollowed screws 102; 104 positioned based on the holes drilled by guide members 112, screws 102; 104 are shown at a predetermined cross angle determined by the surgeon, in accordance with one embodiment of the present disclosure.

After placing the metaphyseal screw 102 in the metaphyseal section 120 and the epiphyseal screw 104 in the epiphyseal section 125, cable 106 is drawn through the hollow structure of the epiphyseal screw 104 and the metaphyseal screw 102 as shown on FIG. 4A. Upon drawing the cable 106 through the length of the metaphyseal screw 102 and the epiphyseal screw 104, the cotter 108 is placed in the metaphyseal screw 102 to lock the cable 106 therein. Referring the FIG. 4B, both ends of cable 106 locked in the first screw 102 using the cotter 108 is shown, in accordance with one exemplary implementation of the present disclosure. Further, referring to FIG. 4C, an axial view of a bone with the screws 102 and 104 positioned at a certain cross angle inside the metaphyseal screw 102 and the epiphyseal screw 104 is shown. The cross angle is determined by the physician depending on the rotational growth correction the patient requires.

Figure 5:
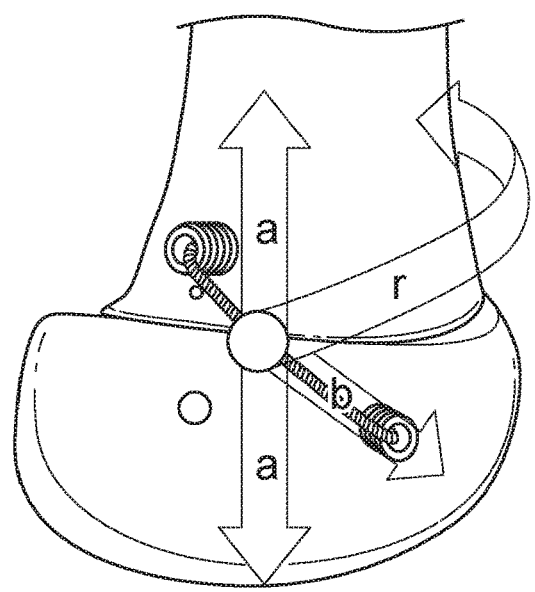
FIG. 5 illustrates torque generated due to growth of bone, in accordance with one embodiment of the present disclosure, the present invention can be seen holding the bone in proper position to help support healthy bone growth.

In use, as bone grows over the time, the implantable device 100 guides the growth of the bone at the physis. As the bone grows, direction of the growth and resulting alignment of the bone is achieved by implantable device 100. In order to explain controlling of the direction and the alignment, FIGS. 5-6D are used for illustration purposes. As known, when the bone grows over the time the physis generates a longitudinal distraction force. When the implantable device 100 is used, the implantable device 100 resists the longitudinal distraction force generated by the growth of the bone of the physis. Specifically, when the bone grows, the longitudinal distraction force pushes the metaphyseal screw 102 and the epiphyseal screw 104 apart such that the cable 106 may act as a tether, thereby generating a torque force. The generation of the torque force leads to rotational growth of the bone. In other words, torque may be generated at distal femoral physis leading to rotation in growth of the bone. Referring to FIG. 5, the torque generated includes a physis distraction force a, resistance b by cable 106, and torque force r. The physis distraction force a occurs due to the growth of the bone over the time. The resistance b occurs due to the strength of the cable 106 applied to resist pull. The torque force r occurs due to the rotation of the bone as a result of the growth begin corrected by the present invention.

Figure 6A:
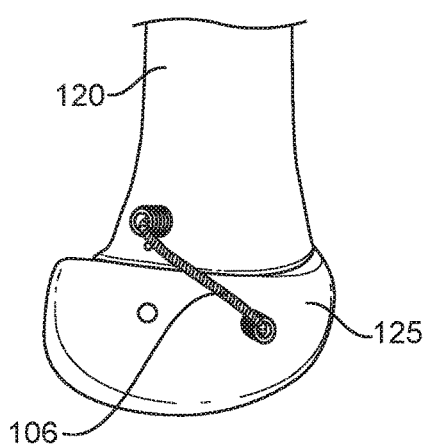
FIGS. 6A, 6B, 6C and 6D illustrate in a sequence the rotational growth of the bone over the time, in accordance with one embodiment of the present disclosure.
Figure 6B:
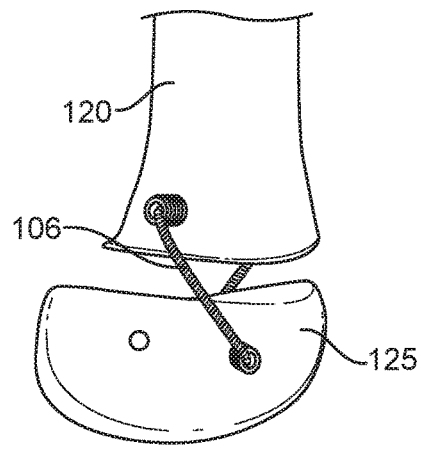
Figure 6C:
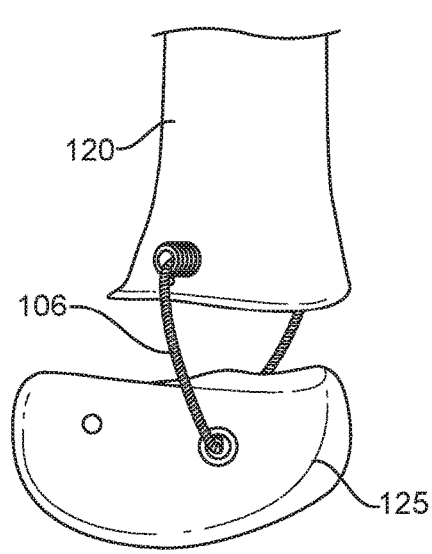
Figure 6D:
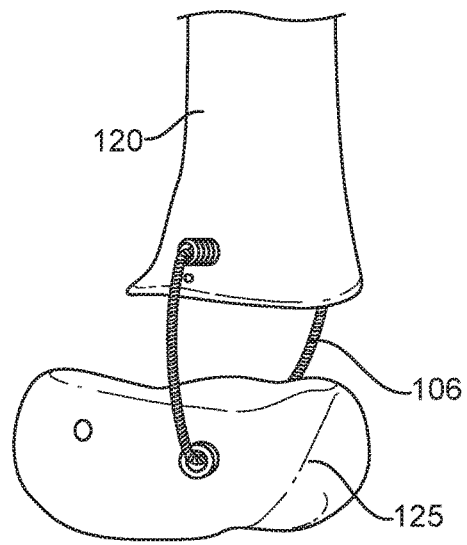

Referring to FIGS. 6A-6D, the rotational growth of the bone over the time is shown. Initially, the physis distraction force a is minimum and the torque force r is high due to position of the metaphyseal screw 102 and the epiphyseal screw 104 (crossing angle). As the growth occurs over the time, as shown in FIG. 6C and FIG. 6D, the torque force r reduces. Specifically, the torque force r reduces until the cable 106 becomes perpendicular to the physis (FIG. 6D). After the cable 106 becomes perpendicular to the physis, the implantable device 100 restricts or reduces longitudinal growth of the bone. This is because, the implantable device 100 applies an opposite force with magnitude equal to the longitudinal growth generated by the physis. Further, upon reaching the absence or minimization of the torque force r, the rotational growth in the bone is considered controlled and the device can removed from a user's body.

In an alternate embodiment of the present disclosure, the implantable device 100 may not include the cotter 108. In order to lock the cable 106 in the first screw 102 or the epiphyseal screw 104, ends of the cable 106 may be tied up thereby avoiding the cotter to lock the guide wire. After passing cable 106 through hollow screws 102; 104 the excess of cable 106 that extends outside the distal ends of screws 102; 104 can be cut by the surgeon.

Figure 7:
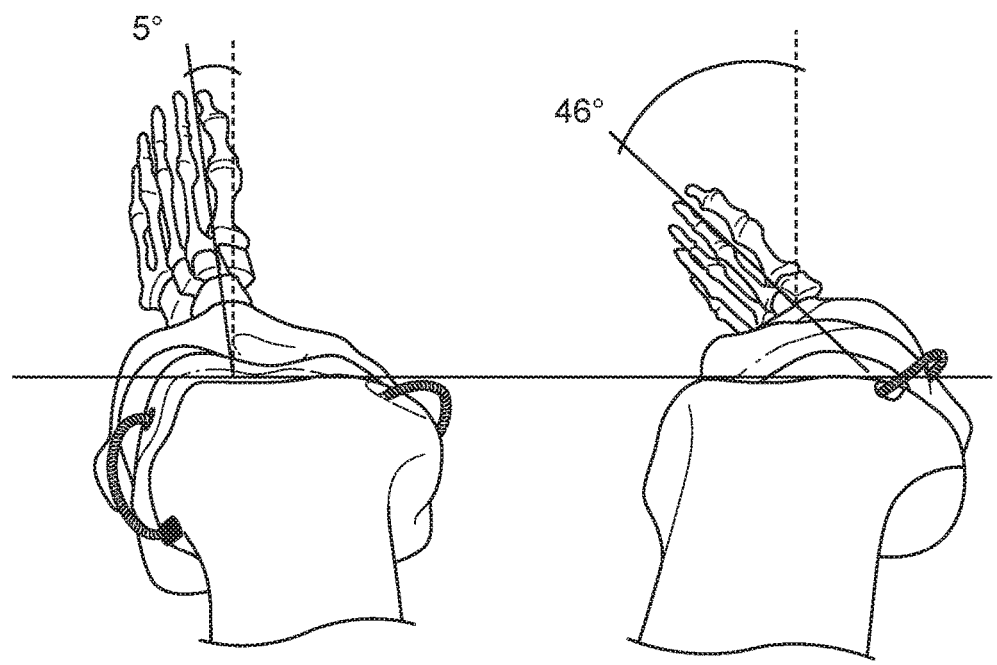
FIG. 7 is an exemplary implementation of the implantable device showing rotational change due to guided growth of the bone in a human lower limb, in accordance with one embodiment of the present disclosure.

Referring to FIG. 7, an example of the subject's bone prior to and after implementing the present disclosure is shown. Left hand side of the FIG. 7 illustrates the magnitude of the rotation achievable in a human lower limb bone model. Upon implementing the implantable device 100, as a result of growth, the bone rotated to 46 degrees, thereby correcting the foot 41 degrees.

Although the present disclosure is explained to correct one type of an angular deformity in the distal femur, it should be understood that the principles described herein can be adapted to other deformities and other bones such as humerus, radius and ulna. Further, the implantable device 100 may be used to treat children or animals by performing a minimum invasive surgery.

The embodiments described herein were tested on calf metacarpals. The calf metacarpals are selected as being similar to adolescent human. The implantable device 100 is implemented on right metacarpal of each metacarpals. At first, the metaphyseal screw 102 and the epiphyseal screw 104 are inserted through the holes created by guiding members 112. Subsequently, cable 106 is drawn through the metaphyseal screw 102 and the epiphyseal screw 104. Then, the excess of cable 106 is cut from the ends of screws 102; 104. Subsequently, cotter 108 is placed in the metaphyseal screw 102 to lock cable 106 in place. Metaphyseal screw 102 and epiphyseal screw 104 are placed at an angle between 25 and 45 in an axial plane (crossing angle).

Each of the calf metacarpals were checked at the end of every month for a period of three months then the implant was removed and the calves were followed up for two years. The rotational growths of the bone of each calf metacarpals are presented in Table 1. Referring to Table. 1, rotational profile measurement evolution of the calf metacarpals is shown.

TABLE 1

Table 1: Rotational profile measurement evolution of the calf metacarpals

| | | Measurement Intervals | | | |
|---|---|---|---|---|---|
| Individuals | Pre-op | 1th Month Post-op | 2nd Month Post-op | 3rd Month Post-op | 2 years Follow up |
| 1 | 0 | 0 | 5 | 28 | 0 |
| 2 | −15 | 3 | 10 | 15 | −3 |
| 3 | −10 | 0 | 5 | 10 | −10 |
| 4 | −3 | 3 | 18 | 20 | −2 |
| 5 | −5 | 5 | 15 | 15 | −5 |
| 6 | −5 | 0 | — | 2 | −5 |
| 7 | −15 | 8 | 10 | 21 | −10 |
| 8 | −13 | 5 | 10 | 15 | 6 |
| Total Average Rotation | −8° | 2.6° | 9.1° | 15.7° | −3.6° |

Table 1 shows measurement intervals of the rotational growth at beginning, $1^{st}$ month, $2^{nd}$ month, $3^{rd}$ month and then after two years since the device was removed. As can be seen from Table 1, the rotational measures for each calf metacarpals are −8, 2.6, 9.1, 15.7, and −3.6 degrees at the beginning, 1st month, $2^{nd}$ month, $3^{rd}$ month and two years, respectively.

In the preceding specification, the present disclosure is described with reference to the specific embodiments. However, it will be apparent to a person with ordinary skill in the art that various modifications and changes can be made, without departing from the scope of the present disclosure. Accordingly, the specification and figures are to be regarded as illustrative examples of the present disclosure, rather than in restrictive sense. All such possible modifications are intended to be included within the scope of present disclosure.

What is claimed is:

1. A method for inserting and implementing an implantable device comprising the steps of:
   a. opening a first small incision into a user's body using guiding members being drilled into a first region of a patient's bone at a predetermined angle depending on the amount of rotational correction needed by a patient;
   b. opening a second small incision into a user's body using guiding members being drilled into a second region of a patient's bone at a predetermined distance and angle with respect to said opening drilled into the first region of a patient's bone in step a;
   c. removing said guiding members;
   d. positioning a hollow first screw in the hole created by said guiding member in the second region;
   e. positioning a hollow epiphyseal screw in the hole created by said guiding member in the epiphyseal region;
   f. inserting a cable through the hollowed portion of said hollow first screw, said first screw and said second screw each having a first and second distal end opposite each other, said cable having a first cable end and a second cable end, said first cable end is passed through said first screw and inserted through said second screw until said first cable end reaches or exceeds the first distal end of said second screw, said second cable end is passed through said first screw and inserted into said second screw through said first distal end and passed through said second screw until said second cable end reaches or exceeds said second distal end.

2. The method of claim 1 comprised of adding the following steps after step h:
   a. inserting a cotter through the first incision and into said hollow first screw to lock said cable therein.

3. The method of claim 1 further including cutting any excess cable extending out of said first or second distal end of said hollow first screw.

* * * * *